(12) United States Patent
McConnell et al.

(10) Patent No.: US 7,371,829 B2
(45) Date of Patent: May 13, 2008

(54) HAPTENS, IMMUNOGENS, ANTIBODIES AND CONJUGATES TO KETAMINE AND ITS METABOLITES

(75) Inventors: Robert Ivan McConnell, Ballymena (GB); Elouard Benchikh, Antrim (GB); Stephen Peter Fitzgerald, Crumlin (GB); John Victor Lamont, Crumlin (GB)

(73) Assignee: Randox Laboratories Limited, Antrim (GB)

(*) Notice: Subject to any disclaimer, the term of this patent is extended or adjusted under 35 U.S.C. 154(b) by 0 days.

(21) Appl. No.: 10/355,348

(22) Filed: Jan. 31, 2003

(65) Prior Publication Data

US 2003/0224447 A1 Dec. 4, 2003

(30) Foreign Application Priority Data

Jan. 31, 2002 (EP) .................................. 02075445

(51) Int. Cl.
*C07K 16/00* (2006.01)
*C07K 16/04* (2006.01)
*C07K 16/13* (2006.01)
*G01N 33/53* (2006.01)
*G01N 33/532* (2006.01)
*G01N 33/533* (2006.01)

(52) U.S. Cl. .................. 530/389.8; 530/403; 530/405; 530/807; 435/7.1; 435/345; 436/56; 436/106; 436/544; 436/546; 436/815; 436/823

(58) Field of Classification Search ............... 435/7.93, 435/961, 4, 7.1, 7.7–7.92, 345, 326; 436/543–546, 436/56, 815–816, 822, 901, 106, 111, 823; 530/387.1, 388.1, 388.9, 389.1, 389.8, 403, 530/405, 807; 424/130.1, 175.1
See application file for complete search history.

(56) References Cited

U.S. PATENT DOCUMENTS

| 4,446,065 A | * | 5/1984 | Lin et al. ................. 530/389.8 |
| 4,469,797 A | * | 9/1984 | Albarella .................... 436/536 |
| 4,533,493 A | * | 8/1985 | Benovic et al. ............. 530/363 |
| 5,051,361 A | * | 9/1991 | Stenglein et al. ............ 435/7.9 |
| 5,096,838 A | * | 3/1992 | Grote et al. ................ 436/536 |
| 5,262,333 A | * | 11/1993 | Heiman et al. ............. 436/537 |
| 5,939,332 A | * | 8/1999 | Lee et al. .................... 436/530 |
| 6,352,863 B1 | * | 3/2002 | Guirguis ..................... 436/534 |
| 2003/0099636 A1 | * | 5/2003 | Epshtein et al. .......... 424/130.1 |

FOREIGN PATENT DOCUMENTS

EP 0 459 387 A2 12/1991

OTHER PUBLICATIONS

Sittampalam, GS. et al. Application of experimental design techniques to optimize a competitive ELISA. Journal or Immunological Methods. 1996, vol. 190, pp. 151-161.*

(Continued)

*Primary Examiner*—Long V. Le
*Assistant Examiner*—Shafiqul Haq
(74) *Attorney, Agent, or Firm*—Blank Rome LLP

(57) ABSTRACT

The invention provides haptens, immunogens comprising such haptens coupled to an antigenicity-conferring carrier material, conjugates comprising such haptens bonded to a labelling agent as well as, antibodies raised against such immunogens and capable of binding with ketamine and its primary metabolite, norketamine.

25 Claims, 12 Drawing Sheets

OTHER PUBLICATIONS

Dotson et al. Ketamine Abuse. Journal of Drug Issues (1995), vol. 25, issue 4.*

Kuby, Janis. Immunology, 1992, W.H. Freeman and Company, p. 125.*

Leung, L.Y. et al., "Comparative Pharmacology in the Rat of Ketamine and Its Two Principal Metabolites, Norketamine and (Z)-6-Hydroxynorketamine", *J. Med. Chem.*, 1986, 29, 2396-2399, XP-002208539.

Owens, S.M. et al., "Antibodies against Arylcyclohexylamines and their Similarities in Binding Specificity with the Phencyclidine Receptor", *J. Pharmacol. Exp. Ther.*, 1988, 246(2), 472-478, XP-008005552.

Owens, S.M. et al., "Molecular Requirements for an Immunological Model of the Phencyclidine Receptor", *Sigma and Phencylidine-Like Compounds as Molecular Probes in Biology*, 1987, 663-672, XP-001077096.

* cited by examiner

Figure-1 Structures of ketamine and its metabolites
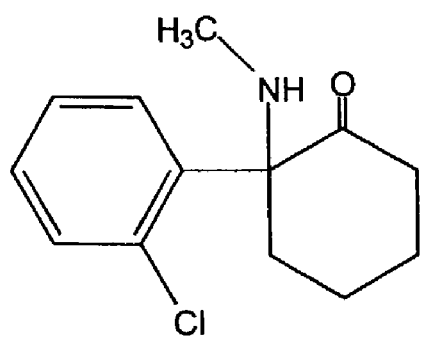
Ketamine
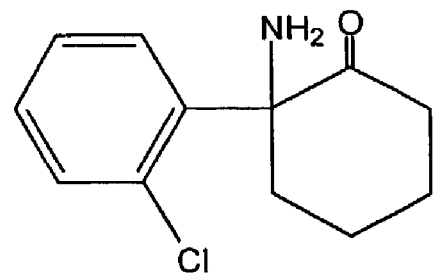
Norketamine
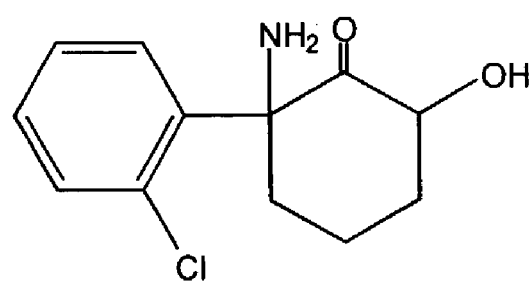
6-Hydroxy norketamine

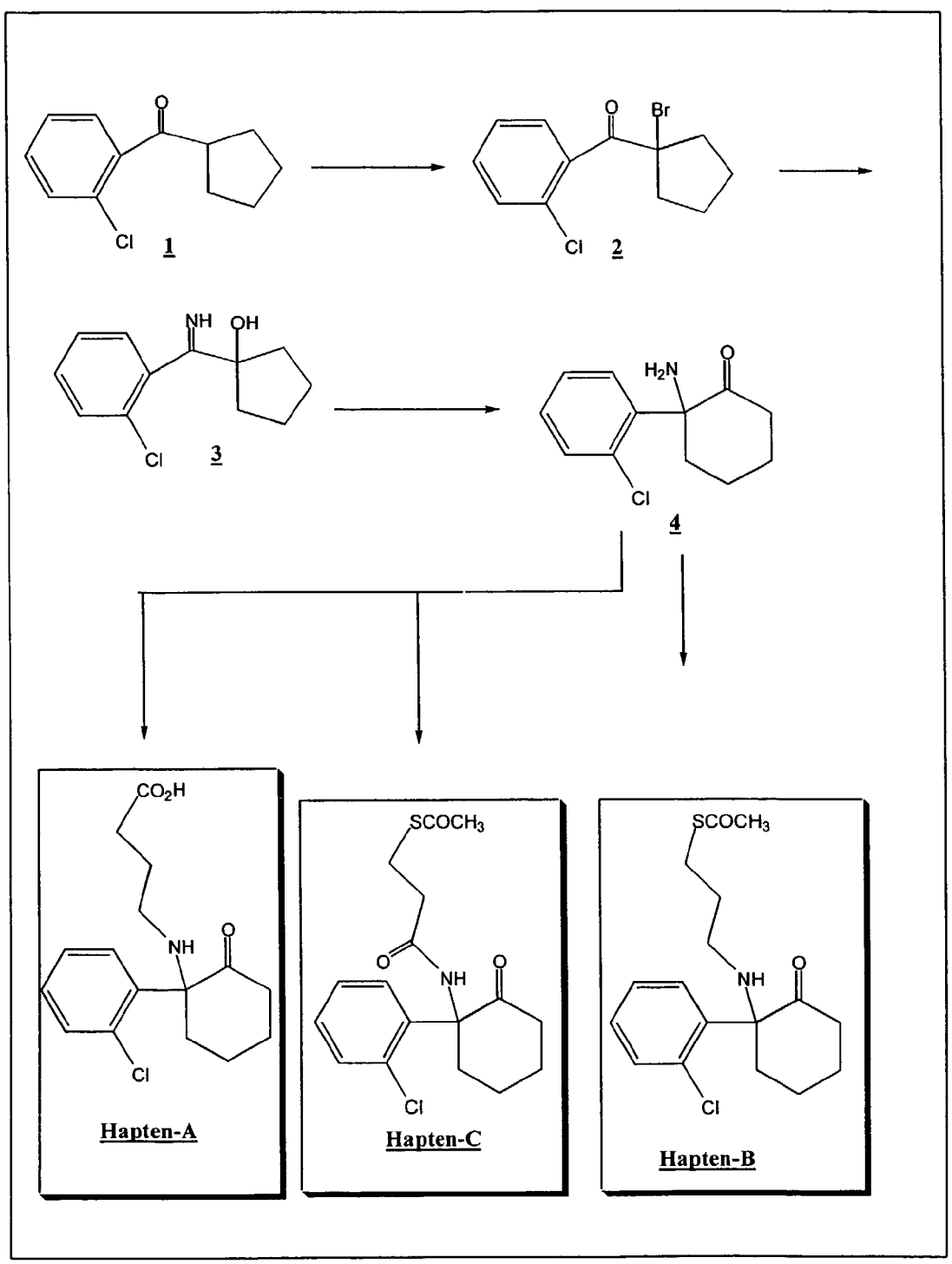
Figure-2: Reaction scheme for the preparation of Haptens A, B and C

Figure-3: Chemical reactions for the preparation of Hapten D
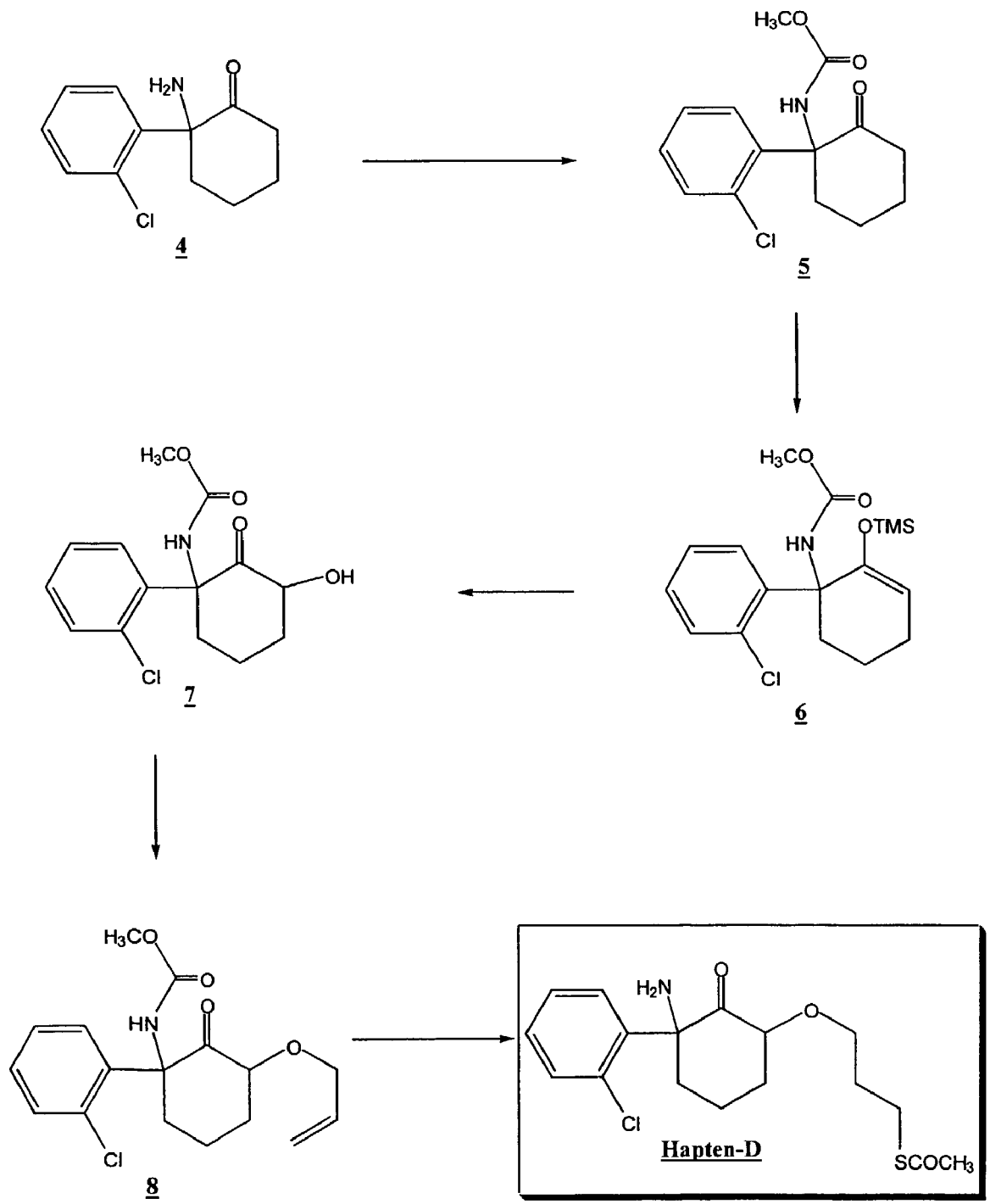

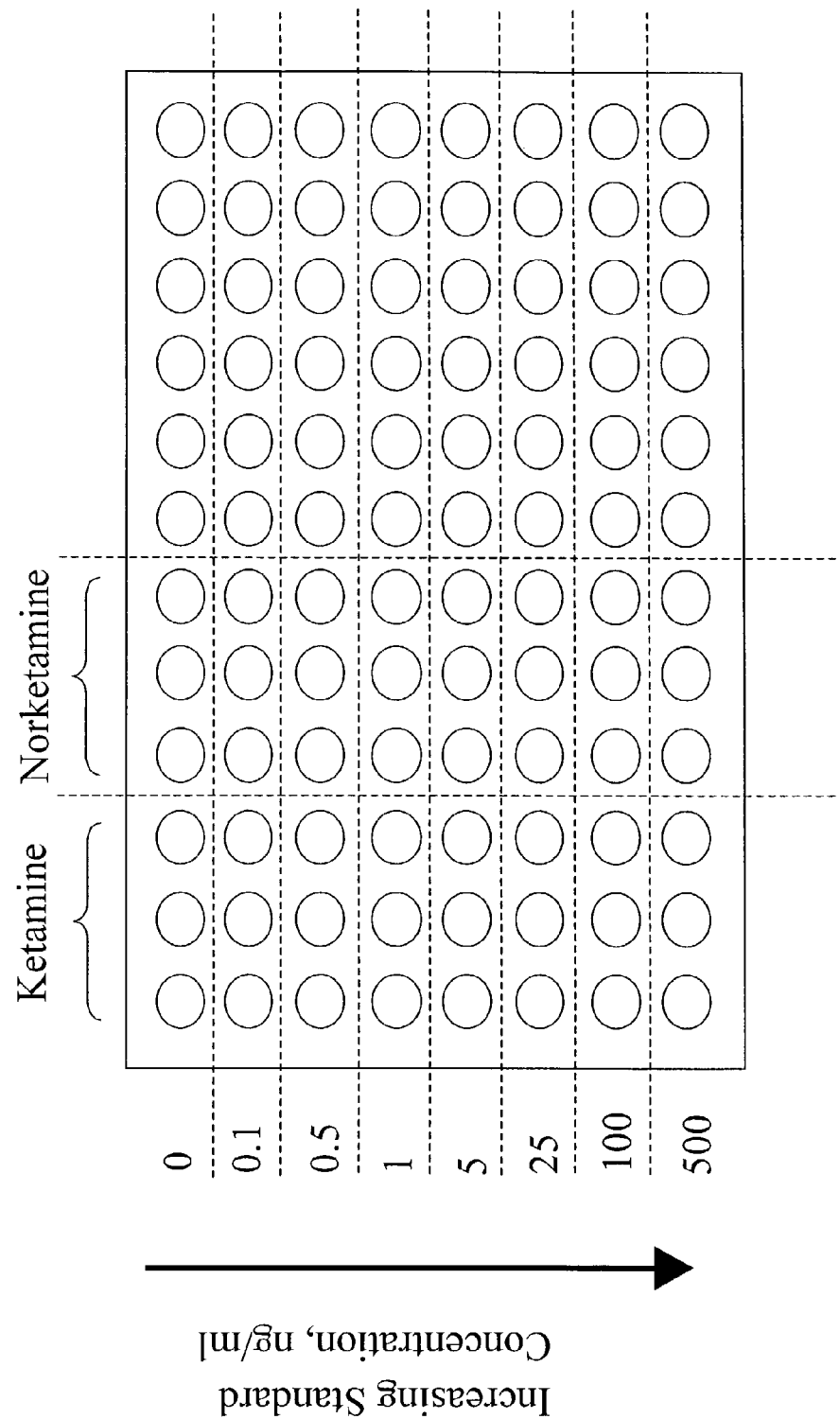
Figure 4: Competitive ELISA Microtiter Plate Assay for Ketamine and Norketamine

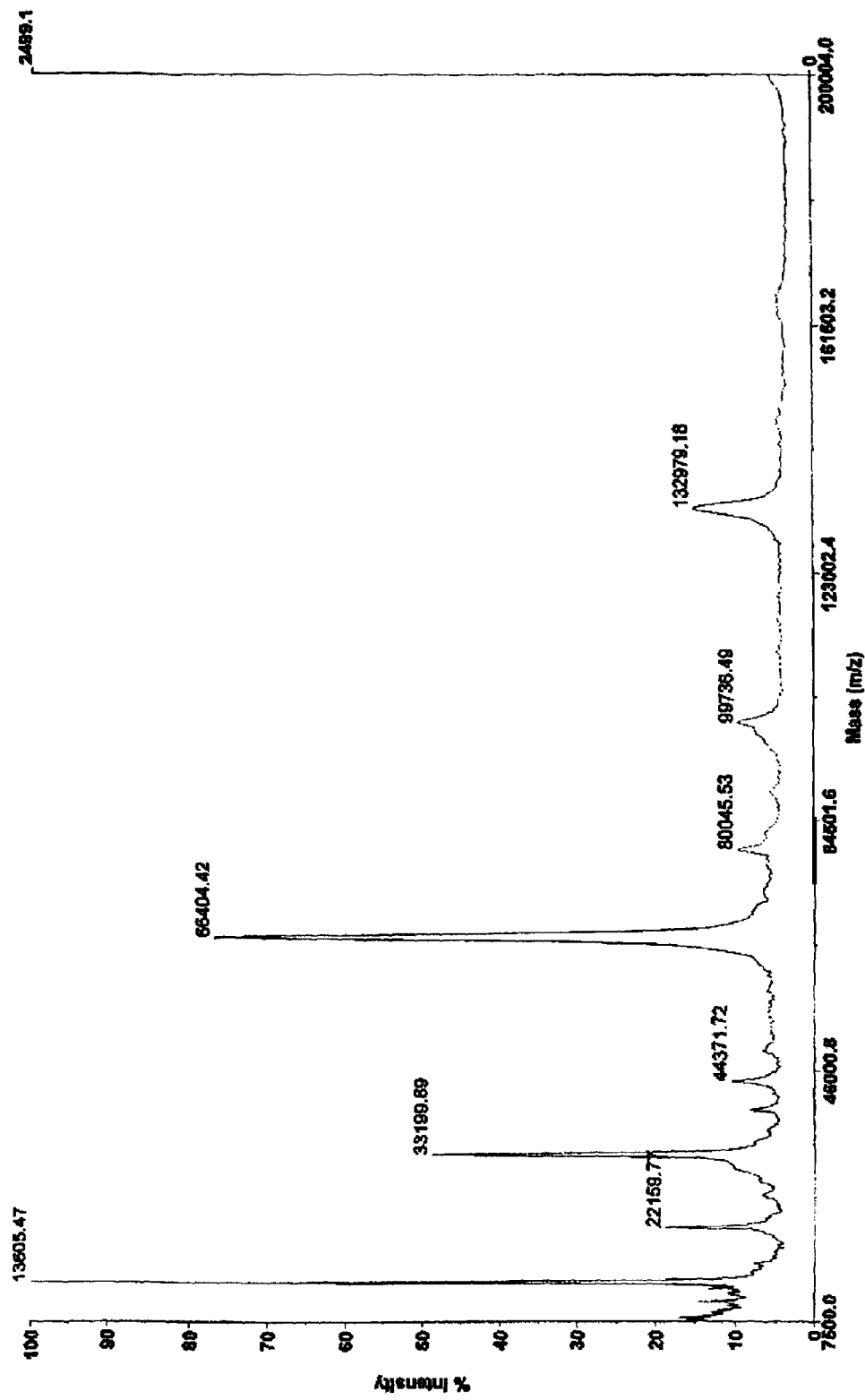
Figure 5: BSA Carrier Material

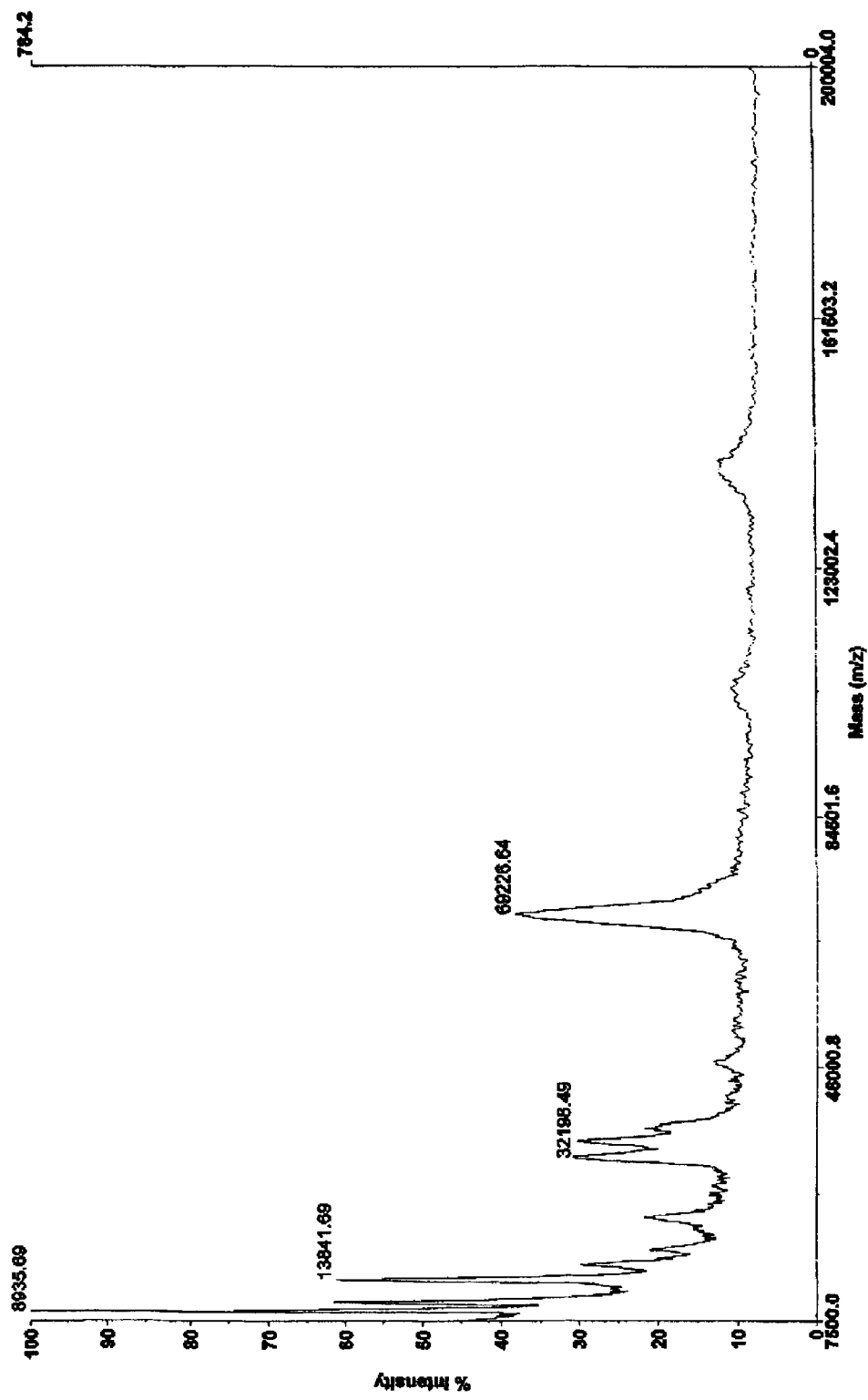
Figure 6: Immunogen A

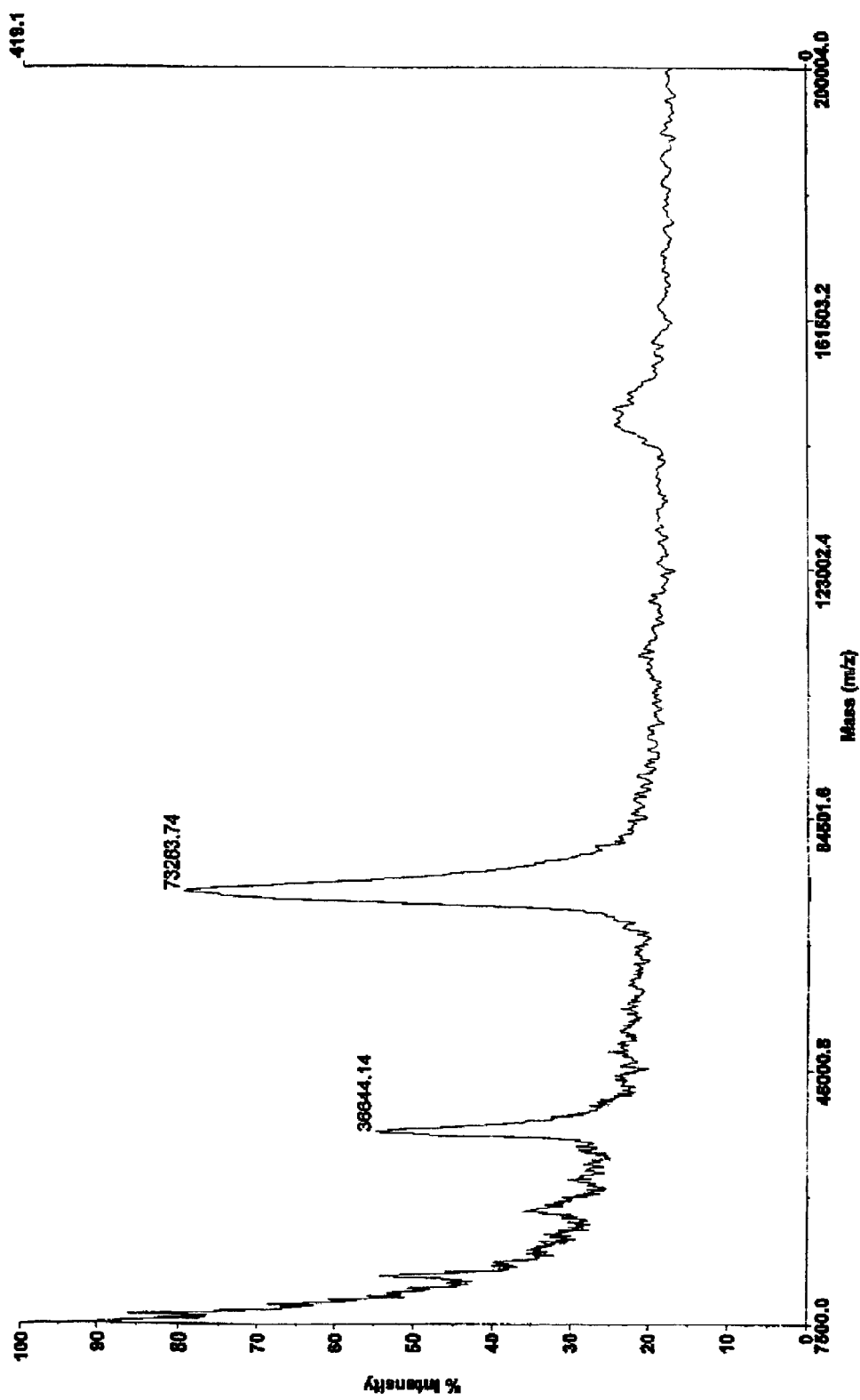
Figure 7: Bromoacetylglycine Modified BSA

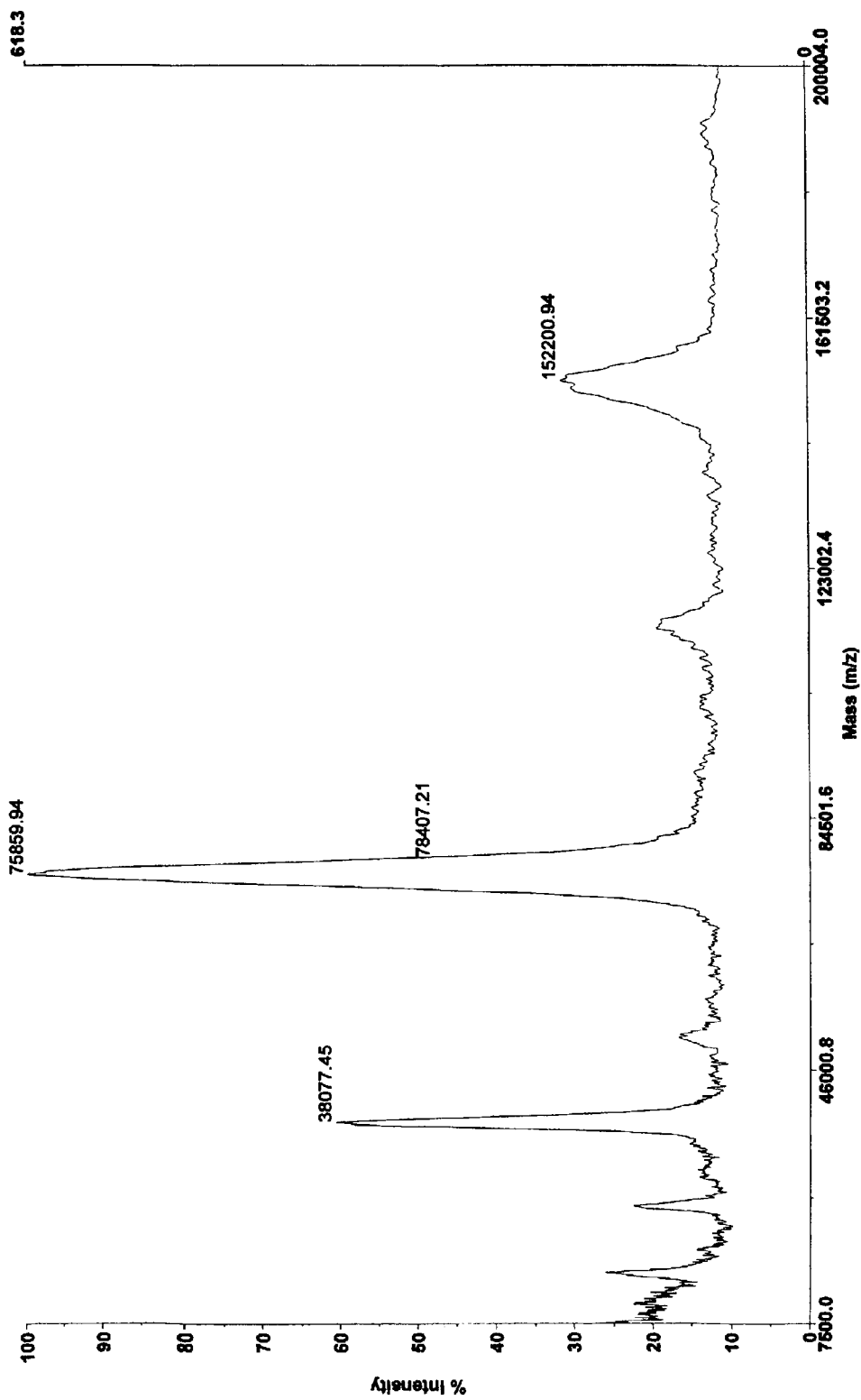
Figure 8: Immunogen B

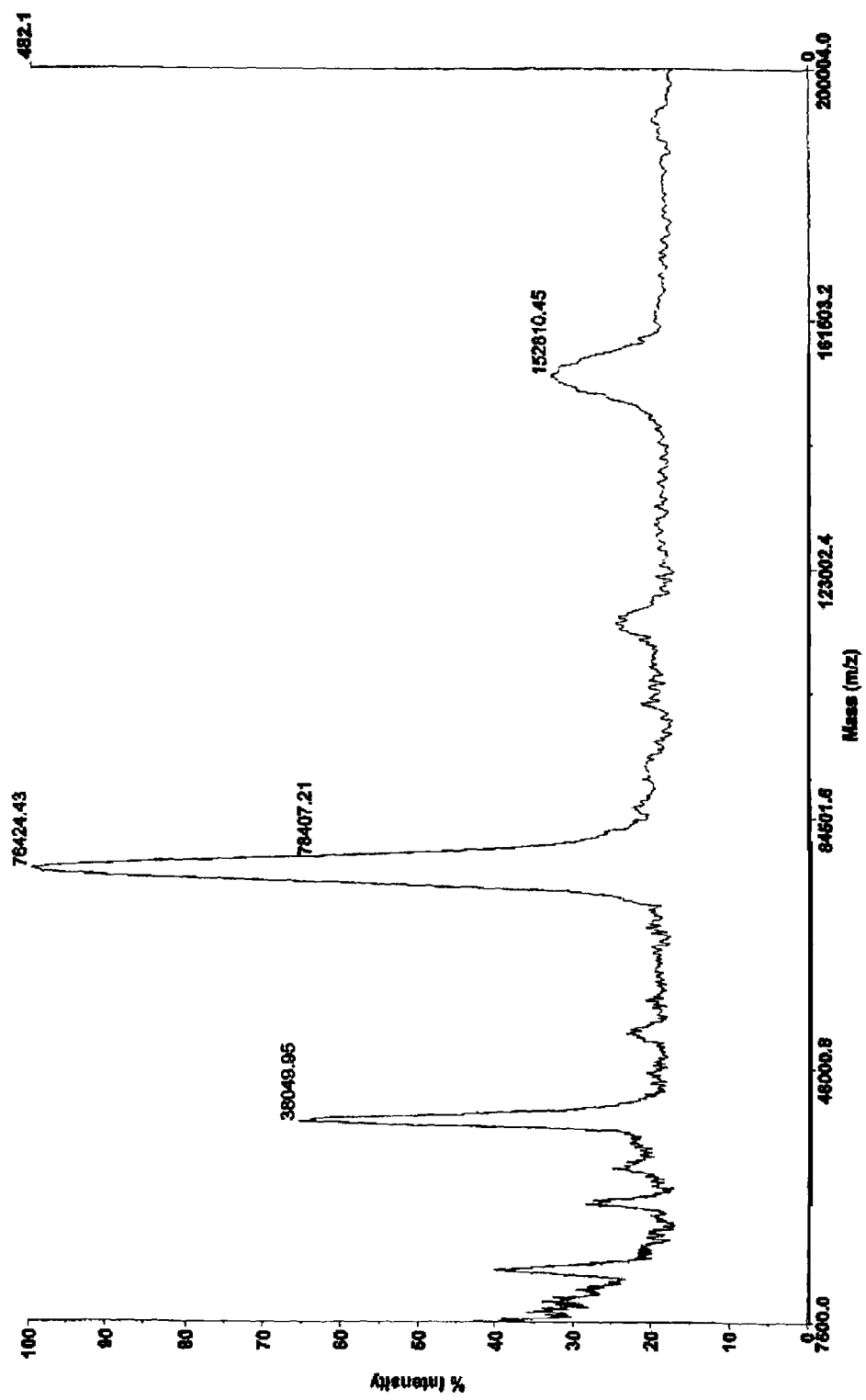
Figure 9: Immunogen C

HAPTENS, IMMUNOGENS, ANTIBODIES AND CONJUGATES TO KETAMINE AND ITS METABOLITES

RELATED APPLICATIONS

This application claims priority from EPO 02075445.3 filed Jan. 31, 2002.

The present invention relates to haptens that are useful for the preparation of immunogens, antibodies and conjugates, for use in competitive immunoassays for the detection of ketamine [(±)-2-(o-chlorophenyl)-2-(methylamino) cyclohexanone] and its primary metabolite, norketamine.

The present invention also relates to a method and kit for detecting or determining ketamine and norketamine.

By "detecting" is meant qualitatively analysing for the presence or absence of a substance.

By "determining" is meant quantitatively analysing for the amount of a substance.

Ketamine (see FIG. 1 of the accompanying drawings) is a short-acting parenteral anaesthetic agent that has been in clinical use for 30 years. The drug causes profound analgesia at subanaesthetic doses and lacks the cardiorespiratory depressive effects associated with most other general anaesthetics. Despite these important clinical advantages, however, disturbing emergence reactions, including delirium and unpleasant dreams, frequently accompany ketamine therapy and limit its clinical usefulness. Although the origin of these adverse central nervous system (CNS) side-effects remains obscure, it has been speculated that metabolites of ketamine may play an important role since circulating concentrations of the parent drug are very low during emergence from ketamine-induced anaesthesia. Ketamine undergoes extensive metabolism by hepatic enzymes, yielding mainly, by N-demethylation, norketamine (see FIG. 1 of the accompanying drawings). This primary amine is metabolised further by hydroxylation of the cyclohexane ring system at the positions 4, 5 and/or 6 to produce a family of hydroxylated norketamines, the predominant member of which is 6-hydroxynorketamine (see FIG. 1 of the accompanying drawings).

PRIOR ART

To date, the determination of ketamine and its metabolites in biological fluids has been based mainly on gas-chromatography-mass spectrometry (GC-MS) and HPLC. These chromatographic methods provide excellent sensitivity and selectivity but require derivatisation of ketamine and its metabolites. These methods are, in addition, too costly and time-consuming for use as screening tools.

Specific binding reactions, such as antibody-antigen interactions, have been used extensively in immunoassays to detect a variety of substances present in biological fluids.

Thus, for example, radioimmunoassays could be used for the determination of ketamine and its metabolites. Radioimmunoassays are very sensitive, but do require radionuclide tracers, for example $^{125}I$ and $^3H$, and in some cases, a preliminary extraction step. There are no known RIAs for ketamine.

Enzyme-linked immunosorbent assays (ELISAs) are a nonradioactive alternative that could be used for the qualitative and quantitative determination of ketamine and its metabolites. Again, there were no known ELISAs for ketamine when priority-forming European Patent Application No. 02075445.3 was filed on Jan. 31, 2002. Since then, Neogen Corporation launched an ELISA kit for ketamine with 100% cross-reactivity to ketamine and 4.6% cross-reactivity to norketamine. It is believed that the Neogen kit uses antibodie and conjugates developed against a ketamine hapten incorporating at least the methylamino epitope of ketamine.

EP 0 459 387 A2 (Abbott Laboratories) describes a fluorescence polarisation assay for phencyclidine and certain phencyclidine derivatives. Phenylcyclohexylamine derivatives are conjugated to carrier materials to produce immunogens and to fluorescein derivatives to produce tracers. Antibodies, preferably monoclonal, are generated to the immunogens. An immunoassay for phencyclidine and phencyclidine derivatives is developed employing the aforementioned antibodies and tracers. This immunoassay exhibits a high degree of specificity to phencyclidine, phencyclidine metabolites and phencyclidine analogs. It does not cross-react significantly with ketamine (see Table 3(c) at page 18). Although the phenylcyclohexylamine derivatives exhibit structural similarity to the haptens of the present invention, the absence of a chloro group on the phenyl ring and of a carbonyl group on the cyclohexyl ring are both significant, as is borne out by the lack of cross-reactivity of the Abbott immunoassay with ketamine.

Owens et al: ('Antibodies against arylcyclohexylamines and their similarities in binding specificity with the phencyclidine receptor' (J. Pharmacol. Exp. Ther. (1988), 246(2), 472-478)) describes antibodies against five epitopes of phencyclidine (PCP)-like molecules, to determine the molecular requirements of arylcyclohexylamine binding to the PCP receptor. Four haptens are synthesised from derivatives of PCP and the TCP analog, namely PCHP; PCHBA; tPPC and TCHP. The fifth hapten is made from phenylcyclohexylamine: PCHAP. These haptens are conjugated to BSA to produce immunogens that are used to generate antibodies. The antibodies produced are highly specific for PCP and some related compounds but exhibit very low cross-reactivity to ketamine (<0.6%) (Table 2, page 475). The hapten PCHAP differs from the haptens of the present invention in that there is no chloro group on the phenyl ring and no carbonyl group on the cyclohexyl ring. The absence of both of these moieties is, again, significant, as is borne out by the lack of cross-reactivity to ketamine.

Owens et al: ('Molecular requirements for an immunological model of the phencyclidine receptor' Sigma and PCP-Like Compounds as Molecular Probes in Biology, 1988) describes the preparation of haptens, immunogens and antibodies to PCP and other arylcyclohexylamines (Table 1, page 667). Four haptens are prepared: PCHP; tPPC; PCHBA and PCHAP (see FIG. 1, page 665). The antibodies generated exhibited high levels of cross-reactivity to PCP and related compounds and low levels of cross-reactivity to ketamine, as indicated by high IC50 values (Table 1, page 667). Once again, the absence of the chloro and carbonyl groups is, again, significant, as is borne out by the lack of cross-reactivity to ketamine.

Leung et al: ('Comparative pharmacology in the rat of ketamine and its two principal metabolites, norketamine and (z)-6-hydroxynorketamine' J. Med. Chem. (1986), 29(11), 2396-2399) describes the synthesis of (z)-6-hydroxynorketamine (a secondary metabolite of ketamine) from norketamine, the primary metabolite of ketamine. They also perform comparative pharmacology studies in rats on ketamine, norketamine and (z)-6-hydroxynorketamine. Leung et al neither discloses nor suggests how to make haptens, immunogens and antibodies to ketamine or norketamine.

SUMMARY OF THE INVENTION

The present invention discloses haptens derivatised with a crosslinker at the N-position of norketamine or at an O-position of a hydroxynorketamine or of a hydroxyketamine.

The invention also provides immunogens comprising such haptens, coupled to an antigenicity-conferring carrier material, as well as, antibodies raised against such haptens. In addition, the invention concerns conjugates comprising such haptens, covalently bonded to a detectable labelling agent.

The invention also provides methods and kits for detecting or determining ketamine and its primary metabolite, norketamine, using conjugates and antibodies of the present invention.

OBJECT OF THE INVENTION

It is an object of the invention to overcome some or all of the disadvantages of the prior art, or to provide an alternative thereto.

BRIEF DESCRIPTION OF DRAWINGS

FIG. 1 shows the structures of ketamine and its metabolites.

FIG. 2 shows a reaction scheme for the preparation of Haptens A, B and C.

FIG. 3 shows chemical reactions for the preparation of Hapten D.

FIG. 4 shows a competitive ELISA microtiter plate assay for ketamine and norketamine.

FIG. 5 shows MALDI-TOF analysis of BSA carrier material.

FIG. 6 shows MALDI-TOF analysis of Immunogen A.

FIG. 7 shows MALDI-TOF analysis of bromoacetyl glycine modified BSA.

FIG. 8 shows MALDI-TOF analysis of Immunogen B.

FIG. 9 shows MALDI-TOF analysis of Tmmunogen C.

DETAILED DESCRIPTION OF THE INVENTION

Figure 10:
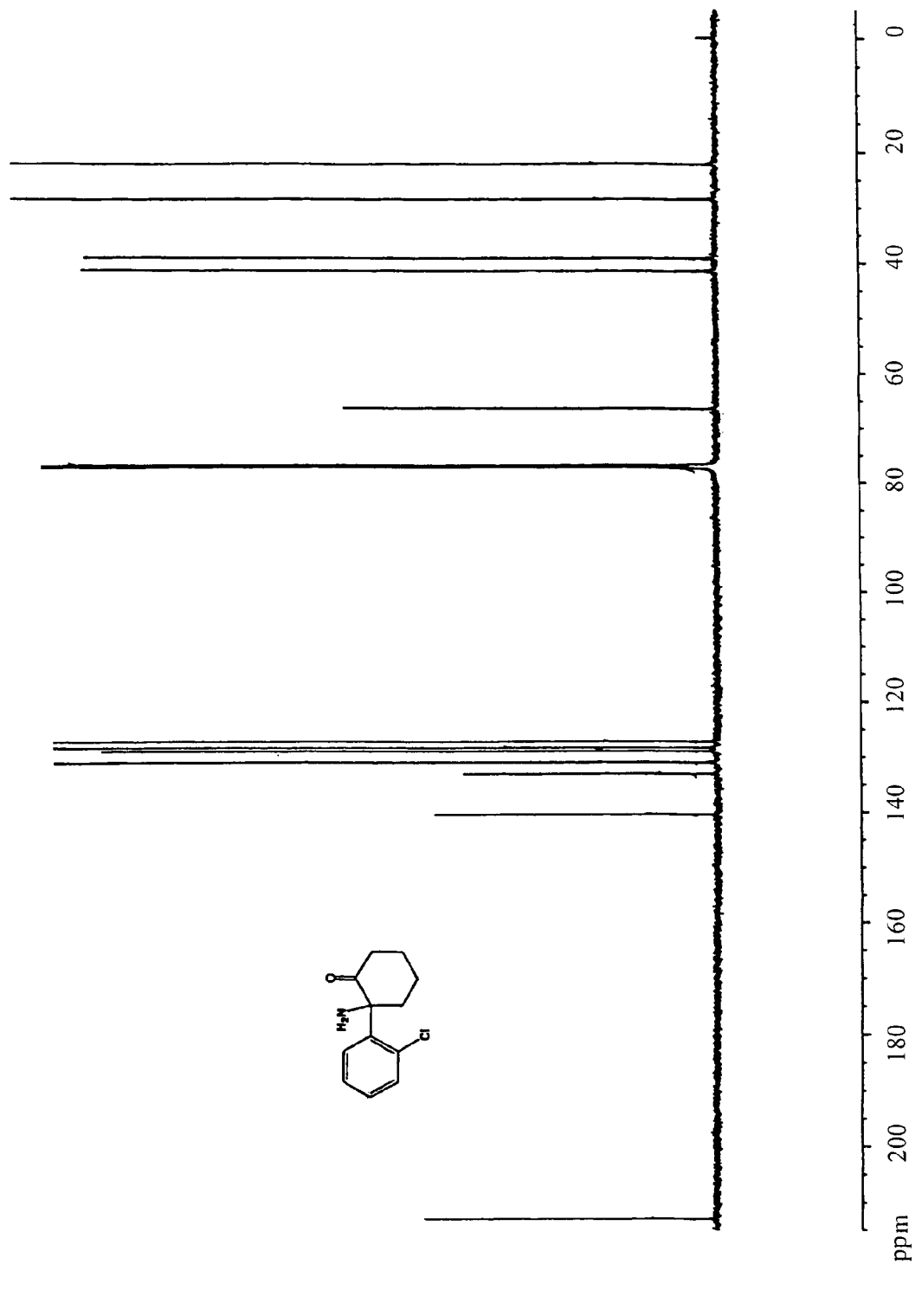
FIG. 10 shows NMR$^{13}$C data for norketamine.

In a first aspect, the present invention provides a hapten derivatised with a crosslinker at the N-position of norketamine.

Preferably, the hapten has the following structural formula:

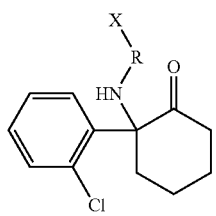

wherein R is a bivalent link and X is a terminal group.

Most preferably, R comprises a substituted or unsubstituted, straight or branched chain, saturated or unsaturated alkylene moiety; and X comprises a carboxylic acid or an ester thereof; an amine, a maleimide, a halocarboxylic acid or an ester thereof, an aldehyde, a dithiopyridyl moiety, a vinylsulphone moiety or a thiocarboxylic acid or an ester thereof.

Thus, in the formula of the preferred embodiment, the crosslinker comprises —R—X. The crosslinker, in the broadest aspect of the invention, may also comprise —R—X.

More preferably, R is a $C_{1-5}$, most preferably a $C_3$, substituted or unsubstituted, straight chain, saturated alkylene moiety.

Most preferably, the substituent, if present, is a carbonyl group.

Advantageously, X is selected from a carboxylic acid, a thiocarboxylic acid, a dithiopyridyl, a maleimide, or an aldehyde moiety. Most advantageously, X is a carboxy (COOH) or thioacetyl (SCOCH$_3$) moiety.

Most advantageously, the hapten is selected from the following hapten derivatives of norketamine: N-(3'-carboxypropyl)norketamine (hapten A); N-(3'-acetylthiopropyl)norketamine (hapten B); and N-(3'-acetylthiopropanoyl)norketamine (hapten C).

These novel haptens are prepared by N-derivatisation, preferably N-alkylation, of norketamine using the appropriate crosslinkers.

The resulting haptens can then be further modified at these functionalised positions for conjugation to modified or non-modified carrier materials to provide immunogens for antibody production and conjugates (tracers) that have excellent sensitivity and specificity for the detection or determination of ketamine and norketamine.

The present invention discloses the preparation of the first hapten derivatives of norketamine. These haptens are employed in the preparation of immunogens by coupling them to modified or non-modified antigenicity-conferring carrier materials. The immunogens obtained are then administered to mammalian hosts to elicit production of specific antibodies, preferably polyclonal antibodies, which are then used to develop competitive immunoassays for ketamine and norketamine, employing haptens conjugated to labelling agents as detection reagents.

The invention also provides an immunogen comprising a hapten of the present invention, coupled to an antigenicity-conferring carrier material. Preferably, the carrier material is a protein, a protein fragment, a synthetic polypeptide or a semi-synthetic polypeptide.

In a still further aspect, the present invention concerns antibodies raised against the immunogen of the present invention, the antibodies being capable of binding with at least one structural epitope of norketamine or ketamine. Preferably, the structural epitope is the arylcyclohexanone moiety, more preferably the chlorophenylcyclohexanone moiety, most preferably the o-chlorophenylcyclohexanone moiety, of ketamine and norketamine.

In a still further aspect, the present invention concerns antibodies having specificity for ketamine characterised by having cross-reactivity of more than 100%, preferably 100-175%, for norketamine.

In a still further aspect, the present invention comprises a conjugate comprising the hapten of the present invention covalently bonded to a detectable labelling agent. Preferably, the labelling agent is selected from an enzyme, a luminescent substance, a radioactive substance, or a mixture thereof More preferably, the labelling agent is an enzyme, preferably a peroxidase, most preferably horseradish peroxidase (HRP). Alternatively, or additionally, the luminescent substance may be a bioluminescent, chemiluminescent or fluorescent material.

The invention further provides a process of preparing the antibodies, the process comprising the steps of immunising an animal, preferably a vertebrate animal, most preferably a mammalian animal, by repeated administration of an immunogen of the present invention, and collecting the resulting serum from the immunised animal. Preferably, the process further comprises fixing said serum antibodies to a backing substrate, preferably a solid support, most preferably a polystyrene solid support. Preferably, the antibodies are polyclonal. Alternatively, the antibodies are monoclonal.

In a still further aspect, the present invention comprises a method for detecting or determining ketamine and norketamine in a sample, the method comprising contacting the sample with the conjugate of the present invention, or a mixture thereof, and with antibodies of the present invention, or a mixture thereof; detecting or determining bound conjugate; and deducing from a calibration curve the presence of, or the amount of, ketamine and norketamine in the sample.

In a further aspect, the invention includes a kit for detecting or determining ketamine and norketamine, the kit including the conjugate of the present invention, or a mixture thereof; and the antibodies of the present invention, or a mixture thereof The kit may optionally include instructions for the use of said conjugates and said antibodies for detecting or determining ketamine and norketamine in a sample.

Preferably, the sample is a solution, such as a biological fluid. More preferably, the sample is serum or urine.

In the method and kit of the present invention, it is preferred that the respective crosslinkers (of the immunogen and the conjugate) are different.

In a further aspect, the present invention involves use of the conjugates of the present invention, or a mixture thereof, with the antibodies of the present invention, or a mixture thereof, to detect or determine ketamine and norketamine in samples such as biological fluids.

Preparation of Haptens

The haptens N-(3'-carboxypropyl)norketamine A, N-(3'-acetylthiopropyl)norketamine B and N-(3'-acetylthiopropanoyl)norketamine C are prepared of FIG. 2 of the accompanying drawings. The bromination of (o-chlorophenyl)cyclopentylketone 1 with bromine in carbon tetrachloride gives a-bromo-(o-chlorophenyl)cyclopentylketone 2. The bromoketone 2 is treated with liquid ammonia to give 1-[(o-chlorophenyl)iminomethyl]cyclopentanol 3. The norketamine 4 is obtained after thermic rearrangement of the alcohol imine 3 at 200° C. The N-alkylation of norketamine 4 by succinic semialdehyde in the presence of sodium cyanoborohydride gives the N-(3'-carboxypropyl)norketamine (Hapten A). The reaction of norketamine 4 with iodopropylthioacetate in ethanolic alkaline solution gives N-(3'-acetylthiopropyl)norketamine (Hapten B). The N-(3'-acetylthiopropanoyl)norketamine (Hapten C) is obtained by reaction of norketamine 4 with 3-acetylthiopropionic acid in DMF in the presence of EDC.hydrochloride and pyridine.

The hapten 6-O-(3'-acetylthiopropyl)norketamine D is prepared in six steps according to FIG. 3 of the accompanying drawings. Norketamine 4 is converted firstly to the methyl carbamate derivative 5 by reaction with methyl chloroformate in benzene at reflux in the presence of sodium carbonate ($Na_2CO_3$). The methyl carbamate 5 is treated with lithium diisopropylamide (LDA) and trimethylsilyl chloride (TMSC) in tetrahydrofuran (THF) at −78° C. to yield the corresponding trimethylsilyl-enol ether 6. The oxidation of 6 with m-chloroperbenzoic acid (MCPBA) in the presence of $Na_2CO_3$ gives the N-protected 6-hydroxynorketamine 7. The O-alkylation of 6 with allyl bromide in alkaline conditions gives the derivative 8. Removal of the methoxycarbonyl-protecting group of 8 by using trimethylsilyl iodide, followed by reaction with thioacetic acid in chloroform at reflux in the presence of 2,2'-azobis(2-methylpropionitrile) (AIBN) catalytic yields the hapten 6-O-(3'-acetylthiopropyl)norketamine D in moderate yield.

Preparation of Immunogens and Conjugates

Although the haptens of the present invention provide defined structural epitopes, they are not in themselves immunogenic and therefore need to be conjugated to carrier materials, which will elicit an immunogenic response when administered to a host animal. Appropriate carrier materials commonly contain poly(amino acid) segments and include polypeptides, proteins and glycoproteins. Illustrative examples of useful carrier materials are bovine serum albumin (BSA), egg ovalbumin, bovine gamma globulin, thyroxin binding globulin, keyhole limpet haemocyanin (KLH) etc. Alternatively, synthetic poly(amino acids) having a sufficient number of available amino groups, such as lysine, may be employed, as may other synthetic or natural polymeric materials bearing reactive functional groups. In particular, carbohydrates, yeasts or polysaccharides may be conjugated to the hapten to produce an immunogen.

Each hapten of the present invention can also be coupled to a labelling agent such as an enzyme (for example, horseradish peroxidase), a substance having fluorescent properties or a radioactive label for the preparation of conjugates (or detection reagents) for use in the immunoassays. The fluorescent substance may be, for example, a monovalent residue of fluorescein or a derivative thereof.

In preparing immunogens or conjugates with haptens of the present invention where a thiol group is present, such as, for example, haptens B, C and D, maleimide, halo or vinylsulphone groups must first be introduced to the carrier material or labelling agent (enzyme or label) using heterobifunctional linkers such as: N-(g-maleimidobutyryloxy) succinimide ester (GMBS); succinimidyl 4-(N-maleimidomethyl)cyclohexane-1-carboxylate (SMCC); (m-maleimidobenzoyl)-N-hydroxysuccinimide (MBS); succinimidyl 4-(p-maleimidophenyl)butyrate (SMPB); N-succinimidyl(4-iodoacetyl)aminobenzoate (SIAB); bromoacetylglycine N-hydroxysuccinimide; N-succinimidyl 3-(2-pyridyldithio)propionate (SPDP); or vinylsulphone (Pierce Chemical Company, USA). The thus-modified carrier material or labelling agent can then be conjugated via the thiol groups on the hapten, for example, haptens B, C and D. For haptens without a thiol group present, such as hapten A, conjugation is performed without prior-modification of the carrier material or labelling agent using standard methods of conjugation such as mixed anhydride, EDC or succinimidyl activation of the hapten.

In order to confirm that adequate conjugation of hapten to carrier material has been achieved, prior to immunisation, each immunogen is evaluated using matrix-assisted UV laser desorption/ionisation time-of-flight mass spectroscopy (MALDI-TOF MS). Each of the immunogens of the present invention is suitable for immunisation, in order to produce antibodies for the detection of ketamine and norketamine.

General Procedure for MALDI-TOF Analysis of Immunogens.

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 µl) were analysed using a matrix of Sinapinic acid and bovine serum albumin (Fluka) was used as an external calibrant. FIG. 5 of the accompanying drawings shows the analysis for BSA carrier material. As will be seen, a major signal was present which indicates an average protonated mass for this sample of m/z 66,404. The signal at m/z 33,200 is consistent with the major component in the doubly-charged form. Further signals were observed including m/z 13,605.

Preparation of Antisera

In order to generate polyclonal antisera, each immunogen of the present invention is mixed with Freund's Adjuvant and the mixture is injected into a host animal, such as rabbit, sheep, mouse, guinea pig or horse. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilised on a solid support, purification steps can be taken to remove undesired material and eliminate non-specific binding.

The specific antibodies prepared in this invention are useful as reagents in immunoassays for the detection or determination of ketamine and norketamine in biological fluids. The antibodies of the present invention are capable of binding with the arylcyclohexanone moiety, preferably the chlorophenylcyclohexanone moiety, most preferably the o-chlorophenylcyclohexanone moiety, of ketamine and of norketamine.

EXAMPLES

Example-1

Preparation of
a-bromo-(o-chlorophenyl)cyclopentylketone 2

To a solution of (o-chlorophenyl)cyclopentyl ketone 1 (21.0 g, 0.1 mol) in 25 ml of anhydrous carbon tetrachloride under inert atmosphere was added, dropwise at 0° C., bromine (16.17 g, 0.1 mol) in 100 ml of carbon tetrachloride, over a period of 30 minutes. After all the bromine had been added, an orange suspension formed. The suspension was stirred for 30 minutes at room temperature and then washed using a 10% (w/v) solution of sodium bisulfite (2×100 ml). The organic phase was dried over anhydrous sodium sulfate, filtered and evaporated under reduced pressure to dryness to give the a-bromo-(o-chlorophenyl)cyclopentyl ketone 2 (24.0 g, 83%) as a dark yellow oil, ready for use without further purification in Example 2.

Example-2

Preparation of
1-[(o-chlorophenyl)iminomethyl]cyclopentanol 3

To a solution of liquid ammonia (100 ml) at −78° C. was added portionwise over 1 hour period the crude compound 2 (24.0 g, 0.0834 mol). The mixture was then stirred for 4 hours and the ammonia allowed to evaporate overnight. The solid residue obtained was suspended in tetrahydrofuran and the precipitate was removed by filtration. The filtrate was concentrated under reduced pressure and the residue obtained triturated with petroleum ether. The resulting precipitate was removed by filtration and dried overnight under $P_2O_5$ to give the free base of 1-[(o-chlorophenyl)iminomethyl] cyclopentanol 3 as a white solid (16.8 g, 90%).

IR (KBr): 3210.9; 1635.9; 763.3 cm$^{-1}$

NMR$^{13}$C (CDCl$_3$): 183.4; 138.2; 130.3; 130.0; 129.8; 127.2; 84.9; 38.6(2C); 23.6(2C) ppm.

M.P. (petroleum ether): 88-90° C.

The 1-[(o-chlorophenyl)iminomethyl]cyclopentanol hydrochloride 3 was prepared by dissolving 20 g (0.089 mol) of the free base of compound 3 in 25 ml of isopropanol and to this solution was added 100 ml of hydrochloric acid (2N) in diethyl ether. The mixture was then stirred for 10 minutes, and the precipitate obtained was filtered, washed by diethyl ether and dried to give a white solid of the hydrochloride of compound 3 (23.14 g, 100%).

M.P.: 144-146° C.

Example-3

Preparation of
[2-amino-2-(o-chlorophenyl)]cyclohexanone
(norketamine) 4

To 250 ml of Dowtherm-A™ at 200° C. was added in one portion the hydrochloride of compound 3 (20 g, 0.077 mol) and the mixture was stirred at 200° C. for 15 minutes. The reaction mixture was then cooled at 110° C., and the precipitate formed was removed and discarded by filtration. The filtrate was diluted in ether and extracted in water (2×200 ml). The combined aqueous phases were washed with ether, made alkaline with 6N sodium hydroxide and extracted in ether (2×150 ml). The combined ether layers were washed with water, dried and concentrated to dryness. The residue obtained was purified by flash chromatography on silica gel (70% hexane/30% ethylacetate) to give norketamine free base (13.75 g, 80%) 4 as a colourless oil.

IR (film): 3381.47; 3310.15; 3064.46; 1939.96; 2864.94; 1712.61 and 757.0.

NMR$^{13}$C (CDCl$_3$): 212.85; 140.47; 133.11; 131.08; 129.01; 128.36; 127.24; 66.52; 41.35; 39.06; 28.42; 22.23 (FIG. 10).

Example-4

Preparation of
N-(3'-carboxypropyl)norketamine-Hapten A

To a 15% solution of succinic semialdehyde (5 ml, 8.018 mmol, 811.7 mg) was added tetrahydrofuran (20 ml), norketamine 4 (1.38 g, 6.17 mmol) and sodium cyanoborohydride (388 mg, 6.17 mmol) at 0° C. The mixture was stirred for two hours at room temperature and thin layer chromatography (10% methanol in chloroform) confirmed that the starting material (norketamine 4) was no longer present. To this solution was added 20 ml of 1 N hydrochloric acid and the reaction mixture was stirred for an additional 1 hour. Tetrahydrofluran was evaporated under reduced pressure and the remaining aqueous solution was neutralised to pH 7 with sodium hydroxide (1N) and extracted in chloroform (3×50 ml). The combined organic layers were washed with 5% sodium bicarbonate solution (50 ml), water (50 ml), dried over anhydrous sodium sulfate, filtered and concentrated to dryness. The residue obtained was purified by chromatographyon silica gel (10% methanol in chloroform) to give 0.8 g (38.8%) of N-(3'-carboxypropyl)norketamine (Hapten A) as a white hygroscopic foam.

IR (film): 3354.76; 3056.10; 1721.05; 1265.70; 736.68

Figure 11:
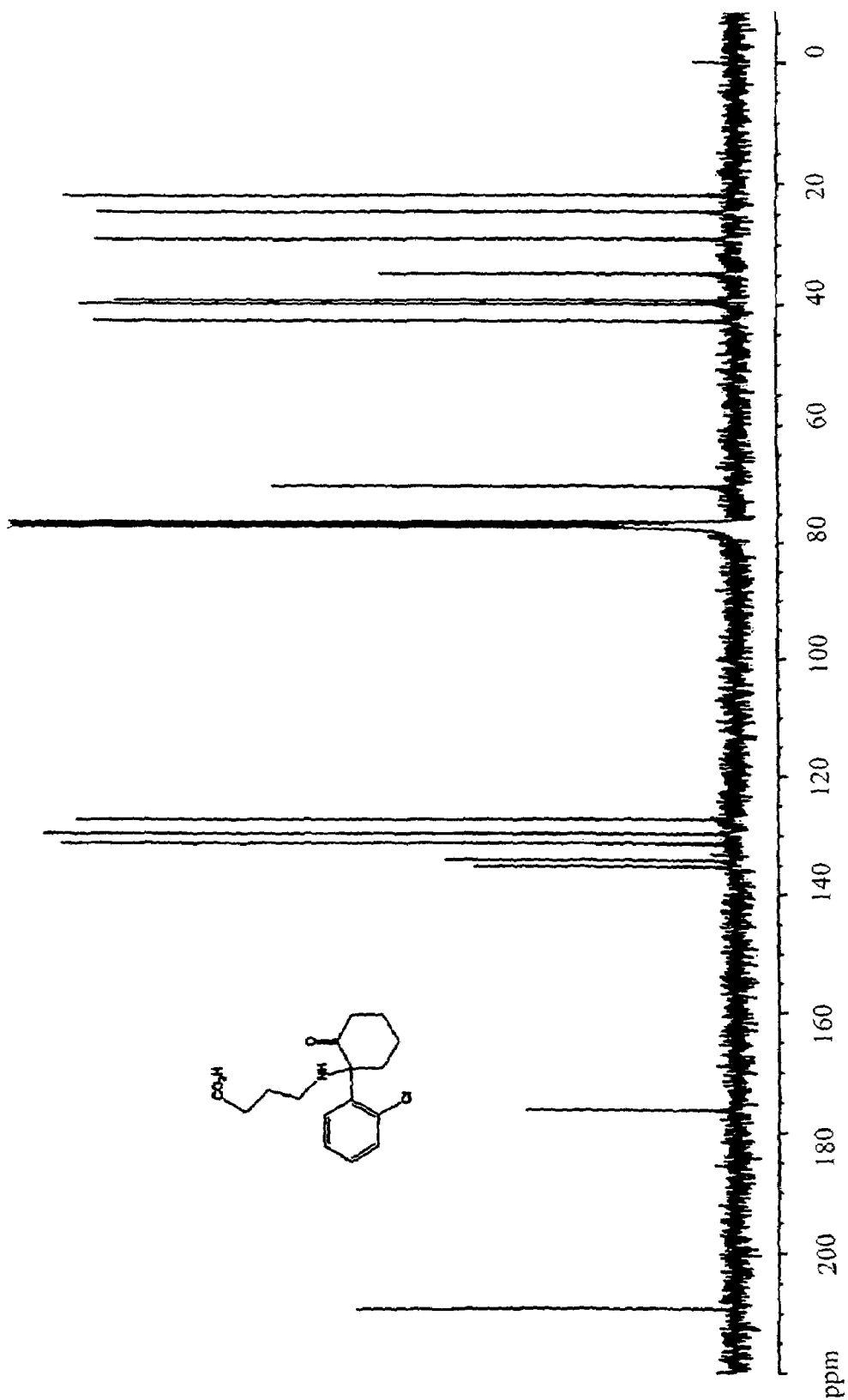
FIG. 11 shows NMR$^{13}$C data for Hapten A.

NMR$^{13}$C (CDCl$_3$): 208.26; 175.37; 135.33; 134.27; 131.47; 129.85; 129.76; 127.08; 70.49; 42.72; 39.02; 38.21; 34.7; 29.01; 24.54; 21.93 (FIG. 11).

Example-5

Preparation of N-(3'-acetylthiopropyl)norketamine-Hapten B

To a solution of norketamine 4 (2.5 g, 0.011 mol) in 50 ml of absolute ethanol was added triethylamine, TEA, (2 ml) and iodopropylthioacetate (2.95 g, 0.0121 mol). The mixture was stirred at reflux for 48 hours (TLC showed that the reaction was complete). The solution was evaporated to dryness and the residue obtained was purified by chromatography on silica gel (60% hexane/40% ethylacetate) to give 1.8 g (48%) of N-(3'-acetylthiopropyl)norketamine (Hapten B) as a clear yellow oil.

IR (film): 3354.33; 3063.62; 2937.2; 2863.86; 1692.95 (br) and 757.97

Figure 12:
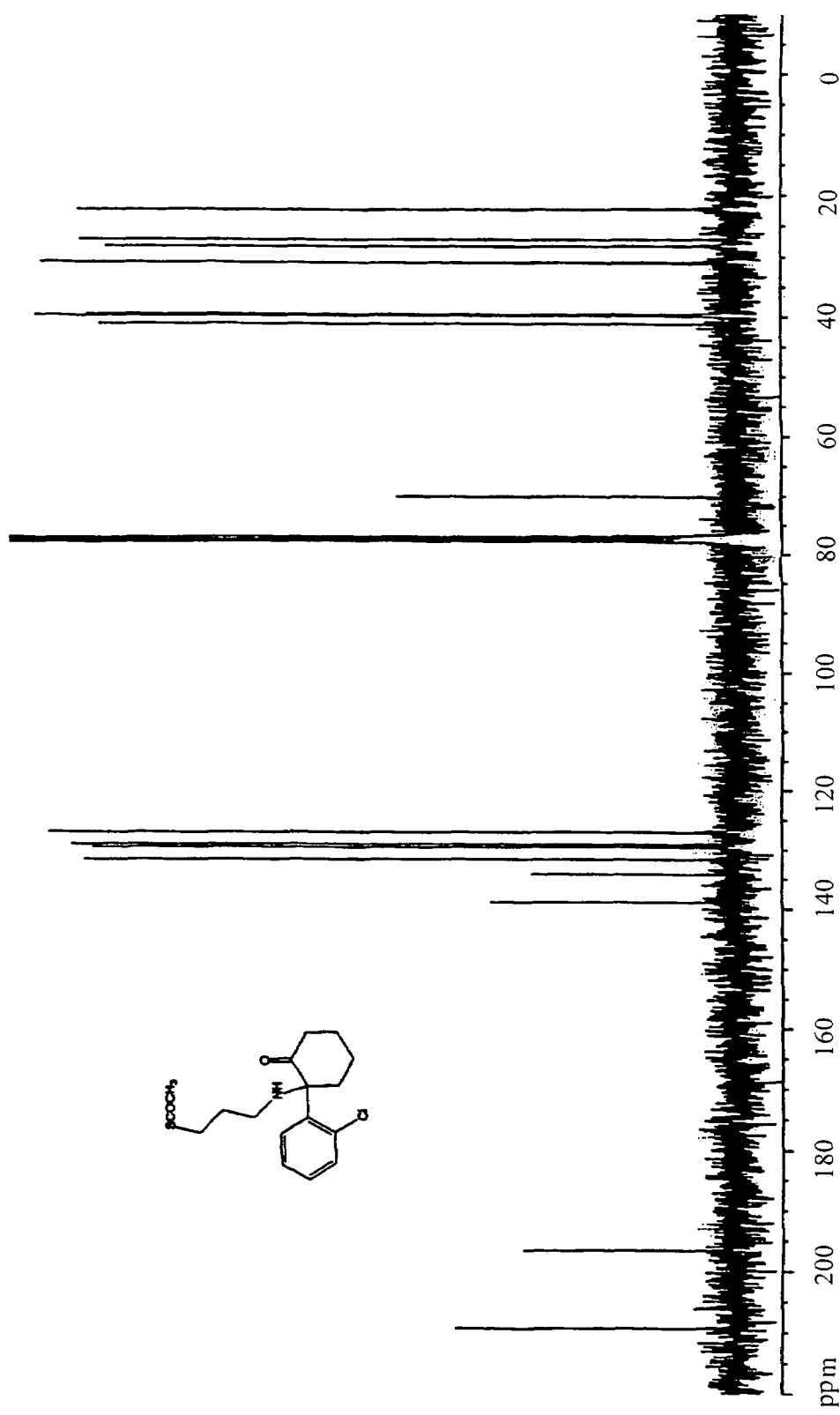
FIG. 12 shows NMR$^{13}$C data for Hapten B.

NMR$^{13}$C (CDCl$_3$): 209.27; 196.51; 138.84; 134.11; 131.6; 129.52; 129.04; 127.06; 70.21; 41.2; 39.83; 39.6; 30.99; 30.92; 28.22; 27.15 and 22.2 (FIG. 12).

Example-6

Preparation of N-(3'-acetylthiopropanoyl)norketamine-Hapten C.

To a solution of norketamine 4 (2.5 g, 0.011 mol) in 10 ml of anhydrous DMF under nitrogen was added 3-acetylthiopropionic acid (1.79 g, 0.012 mol), EDC.hydrochloride (2.53 g, 0,013 mol) and pyridine (1.9 g, 0.024 mol). The mixture was then stirred at room temperature for 2 hours (TLC indicated no starting material left in the reaction). The mixture was evaporated to dryness, and the crude product obtained was purified by flash chromatography on silica gel (50% hexane/50% ethylacetate) to give 2.3 g (62%) of the N-(3'-acetylthiopropanoyl)norketamine (Hapten C) as a yellow oil.

IR (film): 3353.79; 3066.59; 2944.2; 2867.78; 1736.06; 1682 (br) and 760.16.

Example-7

Conjugation of Hapten A to BSA—Immunogen A 104 mg EDC.hydrochloride was dissolved in water (0.5 ml) and immediately added to a solution of hapten A (70 mg, 0.22 mmol) in DMF (1 ml). After mixing, this solution was added to a solution of BSA (200 mg) in 10 ml of water. Sulfo-NHS (52 mg) was immediately added and the reaction mixture was incubated, with stirring at room temperature overnight. The mixture was then dialysed against phosphate buffered saline (PBS), pH 7.2, (3 changes) for 24 hours, and freeze dried.

By MALDI-TOF (see FIG. 6 of the accompanying drawings), a signal was present which indicates an average protonated mass for this sample of m/z 69,227. These data suggest that an average of 9.7 molecules of Hapten A have been conjugated per molecule of BSA.

Example-8

Preparation of Bromoacetylglycine Modified Bovine Serum Albumin

To a solution of BSA (1 g) in 0.1M borate buffer (pH 8.5, 45 ml), cooled to 0° C., was added dropwise N-succinimidyl bromoacetylglycine (0.375 g, 0.13 mmole) in DMF (5 ml). During the addition, the pH was maintained at 8.0 and the solution was stirred at 0° C. for one hour. The pH was adjusted to 7 and the solution was dialysed for 24 hours at 4° C. against distilled water (3 changes). The solution was then freeze dried to give 990 mg of BSA modified by bromoacetylglycine.

By MALDI-TOF (see FIG. 7 of the accompanying drawings), a major signal was present which indicates an average protonated mass for this sample of m/z 73,264. The signal at m/z 36,644 is consistent with the major component in the doubly-charged form. These data suggest that an average of 38.6 lysine groups were modified by the bromoacetylglycine.

Example-9

Conjugation of Hapten B to Bromoacetylglycine Modified BSA—Immunogen B

Hapten B (70 mg) was dissolved in 1 ml of 0.12M potassium carbonate in 80% methanol/20% water, the mixture was then set under nitrogen for 10 to 15 minutes (TLC showed no hapten B left and the formation of a new compound with a lower Rf). Phosphate buffer (1 ml-pH 7) was added to stop the reaction and the pH was adjusted to 7 by the addition of a few drops of 0.5M HCl. This solution was added dropwise to a solution of modified BSA (200 mg in 10 ml of water) and the resulting solution was stirred at 4° C. overnight (protected from light). The solution was dialysed against distilled water for 24 hours (3 changes) and freeze-dried.

By MALDI-TOF (see FIG. 8 of the accompanying drawings), a major signal was present which indicates an average protonated mass for this sample of m/z 75,860. The signal at m/z 38,077 is consistent with the major component in the doubly-charged form. These data suggest that an average of 8.8 molecules of Hapten B have been conjugated per molecule of bromoacetylglycine modified BSA.

Example-10

Conjugation of Hapten C to Bromoacetylglycine Modified BSA—Immunogen C

Hapten C was conjugated to bromoacetylglycine modified BSA using the same method used for hapten B (Example-9).

By MALDI-TOF (see FIG. 9 of the accompanying drawings), a signal was present which indicates an average protonated mass for this sample of m/z 76,424. The signal at m/z 38,050 is consistent with the major component in the doubly-charged form. These data suggest that an average of 10.2 molecules of Hapten C have been conjugated per molecule of bromoacetylglycine modified BSA.

Example-11

Conjugation of Hapten A to HRP—Conjugate A 10 mg EDC.hydrochloride was dissolved in 800 µl of water and immediately added to a solution of 2 mg of hapten A in 200 µl of DMF. After mixing, this solution was added to HRP (20 mg) in 1 ml of water. Sulfo-NHS (5 mg) was immediately added and the reaction mixture was incubated in the dark at room temperature overnight. Excess hapten was removed by desalting with 2 PD-10 columns (Pharmacia) in series, pre-equilibrated with PBS at pH 7.2. The hapten-HRP conjugate was then dialysed overnight against 10L of PBS, pH 7.2, at 4° C.

Example-12

Preparation of Bromoacetylglycine Modified HRP

The preparation of bromoacetylglycine modified HRP was carried out by the same method outlined in Example 8.

Example-13

Conjugation of Hapten B to Bromoacetylglycine Modified HRP—Conjugate B 10 mg of Hapten B was dissolved in 0.5 ml of 0.12M potassium carbonate solution (80% methanol/20% water). The resulting solution was set for 10 min at room temperature. 1 ml of 50 mM phosphate buffer, pH 7, was added to the solution to stop the reaction and the pH was adjusted to 7-7.5 using 0.5M HCl. 500 µl of this solution was added dropwise to a solution of the bromoacetylglycine modified HRP of Example 12 (20 mg in 1 ml of water) and the mixture was stirred in the dark overnight at 4° C. The hapten-HRP conjugate was then purified using two PD-10 columns (Pharmacia Biotechnol), eluted with PBS, pH 7.2, and dialysed overnight against 10L of water.

Example-14

Conjugation of Hapten C to Bromoacetylglycine Modified HRP—Conjugate C

Hapten C was conjugated to bromoacetylglycine modified HRP by the same method used for hapten B in Example-13.

Example-15

Preparation of Antibodies to Immunogen C, Prepared in Example 10

An aqueous solution of the immunogen prepared in Example 10 was formulated with Freund's Complete Adjuvant (FCA) to form an emulsion consisting of 4 mg/ml immunogen in 50% (v/v) FCA. Three sheep were immunised with this emulsion (1° immunisation), 0.25 ml being subcutaneously injected at each of four sites in the flank of each animal. The next immunisation (boost 1) contained 2 mg/ml immunogen and subsequent immunizations (boosts 2 to 11) contained 1 mg/ml immunogen. All boosts were emulsified in 50% (v/v) Freund's Incomplete Adjuvant (FIA) and were administered in the same manner as the 1° immunisation, at monthly intervals for 1 year. Blood sampling took place 7 to 14 days after each boost. Each sample was processed to produce antiserum, which was further purified by caprylic acid and ammonium sulfate precipitation to yield an immunoglobulin G (IgG) fraction. The IgG fraction was evaluated by competitive ELISA microtiter plate assay, as described in Example 16 below.

Example-16

Development of a Competitive ELISA for Ketamine and Norketamine

The wells of an enhanced binding 96 well polystyrene microtiter plate were coated with the IgG fraction of the antiserum raised to immunogen C (hapten C-BSA) (Example 10), diluted in 10 mM Tris, pH 8.5 (125 µl/well). The appropriate antibody coating dilution was determined using standard ELISA checkerboard techniques. The plate was incubated for 2 hours at 37° C., washed 4 times with Tris buffered saline containing Tween 20 (TBST) and tapped dry. Standard solutions of ketamine and norketamine were prepared in TBST at 0, 0.1, 0.5, 1, 5, 25, 100 and 500 ng/ml and 50 µl of each was added to the appropriate wells (FIG. 4). 75 µl of conjugate A (hapten A-HRP) (Example 11), diluted in Tris buffer (pH 7.2) containing EDTA, D-mannitol, sucrose, thimerosal and BSA, was added to each of the wells, as shown in FIG. 4. The appropriate dilution of conjugate was also determined using standard ELISA checkerboard techniques. The plate was incubated at 37° C. for 2 hours. Excess unbound conjugate was removed by washing 6 times over a 10 minute period with TBST.

125 µl of tetramethylbenzidine (TMB) substrate solution was added to each well of the plate that was then incubated for 15 to 20 minutes in the dark at room temperature. The reaction was terminated by addition of 125 µl 0.2M $H_2SO_4$ to each well. The absorbance was then measured at 450 nm using a microtiter plate reader. The data generated in the assay is presented in Table 1 below.

TABLE 1

Data generated from a competitive microtiter plate assay for ketamine and norketamine, employing antiserum raised to immunogen C (hapten C-BSA) (Example 10) and conjugate A (hapten A-HRP) as detection reagent (Example 11).

| Standard Concentration | Ketamine | | Norketamine | |
|---|---|---|---|---|
| ng/ml | $A_{450}$ | % $B/B_0$ | $A_{450}$ | % $B/B_0$ |
| 0 | 2.194 | 100.0 | 2.121 | 100.0 |
| 0.1 | 2.02 | 92.1 | 1.843 | 86.9 |
| 0.5 | 1.817 | 82.8 | 1.416 | 66.8 |
| 1 | 1.489 | 67.9 | 1.368 | 64.5 |
| 5 | 0.935 | 42.6 | 0.961 | 45.3 |
| 25 | 0.548 | 25.0 | 0.482 | 22.7 |
| 100 | 0.404 | 18.4 | 0.320 | 15.1 |
| 500 | 0.254 | 11.6 | 0.222 | 10.5 |
| $IC_{50}$ | 2.9 ng/ml | | 2.1 ng/ml | |
| % CR | 100.0 | | 138.1 | |

$A_{450}$ = absorbance at 450 nm
B = absorbance at 450 nm at x ng/ml standard concentration
$B_0$ = absorbance at 450 nm at 0 ng/ml standard concentration
$IC_{50}$ = standard concentration which produces 50% $B/B_0$
% CR = percentage cross-reactivity based on specificity to ketamine- this is what is meant by the term "cross-reactivity" in the present specification.

Example-17

Cross Reactivity of the Competitive ELISA for Ketamine and Norketamine

In order to determine the specificity of the competitive ELISA for ketamine and norketamine, standard solutions were prepared in TBST at 0, 0.1, 0.5, 1, 5, 25, 100 and 500 ng/ml. Employing each series of standards in the ketamine competitive ELISA, calibration curves were generated and these were used to determine the cross-reactivity of the immunoassay with these substances. The results of this study are presented in Table 2, cross-reactivity of potential cross-reactants phencyclidine and dextromethorphan being calculated according to the following formula:

$$\% \ CR = IC_{50, \ Ketamine} / IC_{50, \ CR} \times 100$$

Where %CR is the percentage cross-reactivity, $IC_{50, \ Ketamine}$ is the concentration of ketamine that causes 50% displacement of signal and $IC_{50, \ CR}$ is the concentration of potential cross-reactant that causes 50% displacement of signal.

TABLE 2

Cross reactivity of the competitive ELISA for ketamine and norketamine

| Cross-Reactant | $IC_{50, \ CR}$ (ng/ml) | % CR |
|---|---|---|
| Phencyclidine | >500.0 | <0.58 |
| Dextromethorphan | >500.0 | <0.58 |

$IC_{50, \ CR}$ = concentration of potential cross-reactant that causes 50% displacement of signal
% CR = percentage cross-reactivity based on specificity to ketamine

What is claimed is:

1. An antibody for use in a method for detecting ketamine and norketamine, said antibody possessing a cross-reactivity of 100-175% for norketamine and a cross-reactivity of 100% for ketamine, wherein said antibody is raised against an immunogen comprising a norketamine hapten, wherein said norketamine hapten is derivatised with a crosslinker at the nitrogen of the norketamine, wherein the norketamine hapten has the following structural formula:

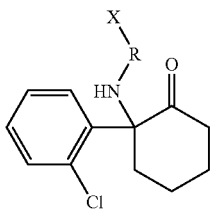

wherein R is a bivalent link and X is a terminal group, wherein R is an alkylene moiety; and X is selected from the group comprising a carboxylic acid or an ester thereof, an amine, a maleimide, a halocarboxylic acid or an ester thereof, an aldehyde, a dithiopyridyl moiety, a vinylsulphone moiety or a thiocarboxylic acid or an ester thereof and said antibody binds at least one structural epitope of each of norketamine and ketamine.

2. The antibody of claim 1, wherein the structural epitope is an arylcyclohexanone moiety.

3. The antibody of claim 2, wherein the structural epitope is a chlorophenylcyclohexanone moiety.

4. A process of preparing the antibody of claim 1, the process comprising the steps of:
immunizing an animal by repeated administration of an immunogen comprising a norketamine hapten wherein said norketamine hapten is derivatised with a crosslinker at the nitrogen of the norketamine, wherein the norketamine hapten has the following structural formula:

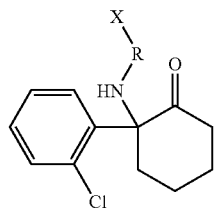

wherein R is a bivalent link and X is a terminal group, wherein R is an alkylene moiety; and X is selected from the group comprising a carboxylic acid or an ester thereof, an amine, a maleimide, a halocarboxylic acid or an ester thereof, an aldehyde, a dithiopyridyl moiety, a vinylsulphone moiety or a thiocarboxylic acid or an ester thereof; and
collecting the resulting serum from the immunized animal.

5. A process of preparing the antibody of claim 1, the process comprising the steps of:
immunizing a vertebrate animal by repeated administration of an immunogen comprising a norketamine hapten wherein said norketamine hapten is derivatised with a crosslinker at the nitrogen of the norketamine, wherein the norketamine hapten has the following structural formula:

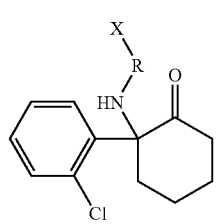

wherein R is a bivalent link and X is a terminal group, wherein R is an alkylene moiety; and X is selected from the group comprising a carboxylic acid or an ester thereof, an amine, a maleimide, a halocarboxylic acid or an ester thereof, an aldehyde, a dithiopyridyl moiety, a vinylsulphone moiety or a thiocarboxylic acid or an ester thereof; and
collecting the resulting serum from the immunized animal.

6. A process of preparing the antibody of claim 1, the process comprising the steps of:
immunizing a mammalian animal by repeated administration of an immunogen comprising a norketamine hapten wherein said norketamine hapten is derivatised with a crosslinker at the nitrogen of the norketamine, wherein the norketamine hapten has the following structural formula:

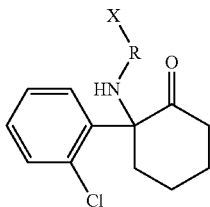

wherein R is a bivalent link and X is a terminal group, wherein R is an alkylene moiety; and X is selected from the group comprising a carboxylic acid or an ester thereof, an amine, a maleimide, a halocarboxylic acid or an ester thereof, an aldehyde, a dithiopyridyl moiety, a vinylsulphone moiety or a thiocarboxylic acid or an ester thereof; and collecting the resulting serum from the immunized animal.

7. A method for detecting ketamine and norketamine in a sample, the method comprising;

contacting the sample with at least one conjugate comprising a norketamine hapten covalently bonded to a detectable labelling agent, wherein said norketamine hapten is derivatised with a crosslinker at the nitrogen of the norketamine, wherein the norketamine hapten has the following structural formula:

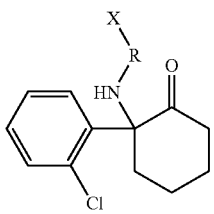

wherein R is a bivalent link and X is a terminal group, wherein R is an alkylene moiety; and X is selected from the group comprising a carboxylic acid or an ester thereof, an amine, a maleimide, a halocarboxylic acid or an ester thereof, an aldehyde, a dithiopyridyl moiety, a vinylsulphone moiety or a thiocarboxylic acid or an ester thereof and at least one antibody of claim 1;

detecting bound conjugate; and deducing from a calibration curve the presence of ketamine and norketamine in the sample.

8. A method for detecting ketamine and norketamine in a sample, the method comprising:

contacting the sample with at least one conjugate comprising a norketamine hapten covalently bonded to a detectable labelling agent, wherein said norketamine hapten is derivatised with a crosslinker at the nitrogen of the norketamine, wherein the norketamine hapten has the following structural formula:

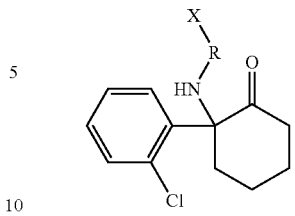

wherein R is a bivalent link and X is a terminal group, wherein R is an alkylene moiety; and X is selected from the group comprising a carboxylic acid or an ester thereof, an amine, a maleimide, a halocarboxylic acid or an ester thereof, an aldehyde, a dithiopyridyl moiety, a vinylsulphone moiety or a thiocarboxylic acid or an ester thereof and at least one antibody of claim 2;

detecting bound conjugate; and deducing from a calibration curve the presence of ketamine and norketamine in the sample.

9. A method for detecting ketamine and norketamine in a sample, the method comprising:

contacting the sample with at least one conjugate comprising a norketamine hapten covalently bonded to a detectable labelling agent, wherein said norketamine hapten is derivatised with a crosslinker at the nitrogen of the norketamine, wherein the norketamine hapten has the following structural formula:

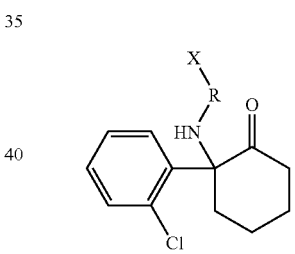

wherein R is a bivalent link and X is a terminal group, wherein R is an alkylene moiety; and X is selected from the group comprising a carboxylic acid or an ester thereof, an amine, a maleimide, a halocarboxylic acid or an ester thereof, an aldehyde, a dithiopyridyl moiety, a vinylsulphone moiety or a thiocarboxylic acid or an ester thereof and at least one antibody of claim 3;

detecting bound conjugate; and deducing from a calibration curve the presence of ketamine and norketamine in the sample.

10. A kit for use in a method for detecting ketamine and norketamine, the kit comprising:

at least one conjugate comprising a norketamine hapten covalently bonded to a detectable labelling agent, wherein said norketamine hapten is derivatised with a crosslinker at the nitrogen of the norketamine, wherein the norketamine hapten has the following structural formula:

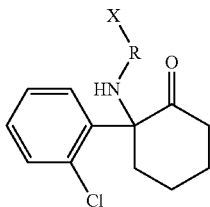

wherein R is a bivalent link and X is a terminal group, wherein R is an alkylene moiety; and X is selected from the group comprising a carboxylic acid or an ester thereof, an amine, a maleimide, a halocarboxylic acid or an ester thereof, an aldehyde, a dithiopyridyl moiety, a vinylsulphone moiety or a thiocarboxylic acid or an ester thereof; and at least one antibody of claim 1.

11. A kit for use in a method for detecting ketamine and norketamine, the kit comprising:

at least one conjugate comprising a norketamine hapten covalently bonded to a detectable labelling agent, wherein said norketamine hapten is derivatised with a crosslinker at the nitrogen of the norketamine, wherein the norketamine hapten has the following structural formula:

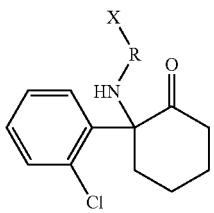

wherein R is a bivalent link and X is a terminal group, wherein R is an alkylene moiety; and X is selected from the group comprising a carboxylic acid or an ester thereof, an amine, a maleimide, a halocarboxylic acid or an ester thereof, an aldehyde, a dithiopyridyl moiety, a vinylsulphone moiety or a thiocarboxylic acid or an ester thereof; and at least one antibody of claim 2.

12. A kit for use in a method for detecting ketamine and norketamine, the kit comprising:

at least one conjugate comprising a norketamine hapten covalently bonded to a detectable labelling agent, wherein said norketamine hapten is derivatised with a crosslinker at the nitrogen of the norketamine, wherein the norketamine hapten has the following structural formula:

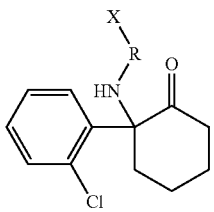

wherein R is a bivalent link and X is a terminal group, wherein R is an alkylene moiety; and X is selected from the group comprising a carboxylic acid or an ester thereof, an amine, a maleimide, a halocarboxylic acid or an ester thereof, an aldehyde, a dithiopyridyl moiety, a vinylsulphone moiety or a thiocarboxylic acid or an ester thereof; and at least one antibody of claim 3.

13. The method of claim 7, wherein said sample is a biological fluid.

14. The antibody of claim 1, wherein said antibody is polyclonal.

15. An antibody for use in a method of detecting ketamine and norketamine, said antibody possessing a cross-reactivity of 100-175% for norketamine and a cross-reactivity of 100% for ketamine, wherein said antibody is raised against an immunogen comprising a norketamine hapten wherein said norketamine hapten is coupled to an antigenicity-conferring carrier material, wherein said norketamine hapten is derivatised with a crosslinker at the nitrogen of the norketamine, wherein the norketamine hapten has the following structural formula:

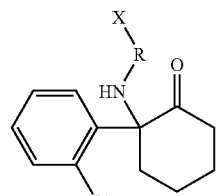

wherein R is a bivalent link and X is a terminal group, wherein R is an alkylene moiety; and X is selected from the group comprising a carboxylic acid or an ester thereof, an amine, a maleimide, a halocarboxylic acid or an ester thereof, an aldehyde, a dithiopyridyl moiety, a vinylsulphone moiety or a thiocarboxylic acid or an ester thereof, wherein said antibody binds at least one structural epitope of each of norketamine and ketamine.

16. A method for detecting ketamine and norketamine in a sample, the method comprising:

contacting the sample with at least one conjugate comprising a norketamine hapten covalently bonded to a detectable labelling agent, wherein said norketamine hapten is derivatised with a crosslinker at the nitrogen of the norketamine, wherein the norketamine hapten has the following structural formula:

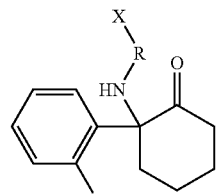

wherein R is a bivalent link and X is a terminal group, wherein R is an alkylene moiety; and X is
selected from the group comprising a carboxylic acid or an ester thereof, an amine, a maleimide, a halocarboxylic acid or an ester thereof, an aldehyde, a dithiopyridyl moiety, a vinylsulphone moiety or a thiocarboxylic acid or an ester thereof and at least one antibody of claim 15;

detecting bound conjugate; and
deducing from a calibration curve the presence of ketamine and norketamine in the sample.

17. A kit for use in a method for detecting ketamine and norketamine, the kit comprising:
at least one conjugate comprising a norketamine hapten covalently bonded to a detectable labelling agent, wherein said norketamine hapten is derivatised with a crosslinker at the nitrogen of the norketamine, wherein the norketamine hapten has the following structural formula:

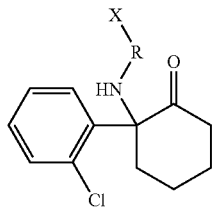

wherein R is a bivalent link and X is a terminal group, wherein R is an alkylene moiety; and X is selected from the group comprising a carboxylic acid or an ester thereof, an amine, a maleimide, a halocarboxylic acid or an ester thereof, an aldehyde, a dithiopyridyl moiety, a vinylsulphone moiety or a thiocarboxylic acid or an ester thereof, wherein the norketamine hapten is prepared by reacting norketamine with an X-R—leaving group; and
at least one antibody of claim 15.

18. A method for detecting ketamine and norketamine in a sample, the method comprising:
contacting the sample with at least one conjugate comprising a norketamine hapten covalently bonded, via a crosslinker, to a detectable labelling agent, wherein said norketamine hapten is derivatised with the crosslinker at the nitrogen of the norketamine, and at least one antibody of claim 1;
detecting bound conjugate; and
deducing from a calibration curve the presence of ketamine and norketamine in the sample.

19. A method for detecting ketamine and norketamine in a sample, the method comprising:
contacting the sample with at least one conjugate comprising a norketamine hapten covalently bonded, via a crosslinker, to a detectable labelling agent, wherein said norketamine hapten is derivatised with the crosslinker at the nitrogen of the norketamine, and at least one antibody of claim 2;
detecting bound conjugate; and
deducing from a calibration curve the presence of ketamine and norketamine in the sample.

20. A method for detecting ketamine and norketamine in a sample, the method comprising:

contacting the sample with at least one conjugate comprising a norketamine hapten covalently bonded, via a crosslinker, to a detectable labelling agent, wherein said norketamine hapten is derivatised with the crosslinker at the nitrogen of the norketamine, and at least one antibody of claim 3;
detecting bound conjugate; and
deducing from a calibration curve the presence of ketamine and norketamine in the sample.

21. A kit for use in a method for detecting ketamine and norketamine, the kit comprising:
at least one conjugate comprising a norketamine hapten covalently bonded, via a crosslinker, to a detectable labelling agent, wherein said norketamine hapten is derivatised with the crosslinker at the nitrogen of the norketamine; and
at least one antibody of claim 1.

22. A kit for use in a method for detecting ketamine and norketamine, the kit comprising:
at least one conjugate comprising a norketamine hapten covalently bonded, via a crosslinker, to a detectable labelling agent, wherein said norketamine hapten is derivatised with the crosslinker at the nitrogen of the norketamine; and
at least one antibody of claim 2.

23. A kit for use in a method for detecting ketamine and norketamine, the kit comprising:
at least one conjugate comprising a norketamine hapten covalently bonded, via a crosslinker, to a detectable labelling agent, wherein said norketamine hapten is derivatised with the crosslinker at the nitrogen of the norketamine; and
at least one antibody of claim 3.

24. A method for detecting ketamine and norketamine in a sample, the method comprising:
contacting the sample with at least one conjugate comprising a norketamine hapten covalently bonded, via a crosslinker, to a detectable labelling agent, wherein said norketamine hapten is derivatised with the crosslinker at the nitrogen of the norketamine, and at least one antibody of claim 15;
detecting bound conjugate; and
deducing from a calibration curve the presence of ketamine and norketamine in the sample.

25. A kit for use in a method for detecting ketamine and norketamine, the kit comprising:
at least one conjugate comprising a norketamine hapten covalently bonded, via a crosslinker, to a detectable labelling agent, wherein said norketamine hapten is derivatised with the crosslinker at the nitrogen of the norketamine; and
at least one antibody of claim 15.

* * * * *